US012156542B2

(12) United States Patent
Alshaiba Saleh Ghannam Almazrouei et al.

(10) Patent No.: US 12,156,542 B2
(45) Date of Patent: Dec. 3, 2024

(54) PERSONAL ULTRASONIC ATOMIZER DEVICE ABLE TO CONTROL THE AMOUNT OF LIQUID FLOW

(71) Applicant: SHAHEEN INNOVATIONS HOLDING LIMITED, Abu Dhabi (AE)

(72) Inventors: Mohammed Alshaiba Saleh Ghannam Almazrouei, Abu Dhabi (AE); Imad Lahoud, Abu Dhabi (AE)

(73) Assignee: Shaheen Innovations Holding Limited, Abu Dhabi (AE)

( * ) Notice: Subject to any disclaimer, the term of this patent is extended or adjusted under 35 U.S.C. 154(b) by 457 days.

(21) Appl. No.: 17/435,483

(22) PCT Filed: Jun. 20, 2019

(86) PCT No.: PCT/IB2019/055192

§ 371 (c)(1),
(2) Date: Sep. 1, 2021

(87) PCT Pub. No.: WO2020/254862

PCT Pub. Date: Dec. 24, 2020

(65) Prior Publication Data

US 2022/0132935 A1 May 5, 2022

(51) Int. Cl.
*A24F 40/485* (2020.01)
*A24F 40/42* (2020.01)
(Continued)

(52) U.S. Cl.
CPC ............ *A24F 40/485* (2020.01); *A24F 40/42* (2020.01); *A24F 40/46* (2020.01); *A24F 40/65* (2020.01)

(58) Field of Classification Search
CPC ........ A24F 40/485; A24F 40/46; A24F 40/42; A24F 40/40
See application file for complete search history.

(56) References Cited

U.S. PATENT DOCUMENTS 4,119,096 A 10/1978 Drews
4,334,531 A 6/1982 Reichl
(Continued)

FOREIGN PATENT DOCUMENTS

CN 2648836 Y 10/2004
CN 101648041 A 2/2010
(Continued)

OTHER PUBLICATIONS

European Search Report mailed Dec. 1, 2022 for co-pending European application No. 19933337.8.
(Continued)

*Primary Examiner* — Hae Moon Hyeon
(74) *Attorney, Agent, or Firm* — Amedeo F. Ferraro, Esq.

(57) ABSTRACT

The invention relates to a personal ultrasonic atomizer device (10), which includes a cartridge (12) having a reservoir (26) for holding a liquid to be atomized, which is interchangeable prior to complete discharging of the reservoir (26) and includes an anti-tamper and anti-counterfeiting safeguard, a sonication chamber (14), placed in fluid communication with the reservoir (26), and for cavitating a liquid placed in contact with a piezoelectric oscillation piece (112); such that vape (V) and/or mist is generated without combustion and/or heating of the liquid, where the personal ultrasonic atomizer device (10) includes a liquid retention material (76) for allowing use of the personal ultrasonic atomizer device (10) in any orientation, and where the personal ultrasonic atomizer device (10) is controllable by an external electronic device.

20 Claims, 8 Drawing Sheets

(51) Int. Cl.
*A24F 40/46* (2020.01)
*A24F 40/65* (2020.01)

(56) References Cited

U.S. PATENT DOCUMENTS 5,355,873 A 10/1994 Del Bon
5,518,179 A 5/1996 Humberstone et al.
5,551,416 A 9/1996 Stimpson
5,894,841 A 4/1999 Voges
5,950,619 A 9/1999 van der Linden
6,011,345 A 1/2000 Murray
6,040,560 A 3/2000 Fleischhauer
6,402,046 B1 6/2002 Loeser
6,601,581 B1 8/2003 Babaev
6,679,436 B1 1/2004 Onishi
7,129,619 B2 10/2006 Yang
8,991,722 B2 3/2015 Friend
9,242,263 B1 1/2016 Copeman
9,278,365 B2 3/2016 Banco
9,415,412 B2 8/2016 Kawashima
9,687,029 B2 6/2017 Liu
9,687,627 B2 6/2017 Gallem
9,718,078 B1 8/2017 Chau
9,867,398 B2 1/2018 Guo
9,980,140 B1 5/2018 Spencer
10,034,495 B2 7/2018 Alarcon
10,071,391 B2 9/2018 Yu
10,195,368 B2 2/2019 Wang
10,300,225 B2 5/2019 Terry
10,327,479 B2 6/2019 Popplewell
10,328,218 B2 6/2019 Reed
10,412,996 B2 * 9/2019 Bright .................... A24F 40/48
10,506,827 B2 12/2019 Liu
10,561,803 B2 2/2020 Liu
10,617,150 B2 4/2020 Cameron
10,701,976 B2 * 7/2020 Verleur ................ A61M 15/06
10,757,971 B2 9/2020 Liu
11,039,641 B2 6/2021 Liu
11,207,711 B2 12/2021 Hejazi
11,219,245 B2 1/2022 Liu
11,278,055 B2 3/2022 Liu
11,304,451 B2 4/2022 Hejazi
11,324,253 B2 5/2022 Liu
11,431,242 B2 8/2022 Liu
11,517,685 B2 12/2022 Danek
11,589,609 B2 2/2023 Liu
11,641,876 B2 5/2023 Liu
11,690,963 B2 7/2023 Danek
11,700,881 B2 7/2023 Liu
11,730,896 B2 8/2023 Hutchins
11,744,282 B2 9/2023 Liu
11,744,284 B2 9/2023 Liu
11,771,133 B2 10/2023 Lin
11,771,137 B2 10/2023 Liu
11,796,732 B2 10/2023 Novak, III
11,877,600 B2 1/2024 Liu
11,964,301 B2 4/2024 Hejazi
2002/0129813 A1 9/2002 Litherland
2003/0192532 A1 10/2003 Hopkins
2003/0209005 A1 11/2003 Fenn
2006/0243277 A1 11/2006 Denyer
2007/0125370 A1 6/2007 Denyer
2008/0054091 A1 3/2008 Babaev
2008/0088202 A1 4/2008 Duru
2008/0156320 A1 7/2008 Low
2008/0164339 A1 7/2008 Duru
2009/0022669 A1 1/2009 Waters
2009/0065600 A1 3/2009 Tranchant
2010/0084488 A1 4/2010 Mahoney, III
2010/0139652 A1 6/2010 Lipp
2012/0126041 A1 5/2012 Mahito et al.
2013/0220315 A1 8/2013 Conley
2014/0007864 A1 1/2014 Gordon
2014/0151457 A1 6/2014 Wilkerson
2014/0261414 A1 9/2014 Weitzel
2014/0270727 A1 9/2014 Ampolini
2015/0069146 A1 3/2015 Lowy
2015/0202387 A1 7/2015 Yu
2015/0230522 A1 8/2015 Horn
2015/0231347 A1 8/2015 Gumaste
2015/0272214 A1 10/2015 Giller
2016/0001316 A1 1/2016 Friend
2016/0066619 A1 3/2016 Di Carlo
2016/0089508 A1 3/2016 Smith
2016/0199594 A1 7/2016 Finger
2016/0206001 A1 7/2016 Eng
2016/0213866 A1 7/2016 Tan
2016/0264290 A1 9/2016 Hafer
2016/0324212 A1 11/2016 Cameron
2016/0338407 A1 11/2016 Kerdemelidis
2017/0042242 A1 2/2017 Hon
2017/0119052 A1 5/2017 Williams
2017/0119059 A1 5/2017 Zuber
2017/0135411 A1 5/2017 Cameron
2017/0136194 A1 5/2017 Cameron
2017/0136484 A1 5/2017 Wilkerson
2017/0172210 A1 * 6/2017 Bright .................... A24F 40/48
2017/0251718 A1 9/2017 Armoush
2017/0265521 A1 9/2017 Do
2017/0281883 A1 10/2017 Li
2017/0303594 A1 10/2017 Cameron
2017/0368273 A1 12/2017 Rubin
2018/0042306 A1 2/2018 Atkins
2018/0153217 A1 6/2018 Liu
2018/0160737 A1 6/2018 Verleur
2018/0166981 A1 6/2018 Leppard
2018/0192702 A1 7/2018 Li
2018/0269867 A1 9/2018 Terashima
2018/0029677 A1 10/2018 Terry
2018/0286207 A1 10/2018 Baker
2018/0296777 A1 10/2018 Terry
2018/0296778 A1 10/2018 Hacker
2018/0310625 A1 11/2018 Alarcon
2018/0338532 A1 11/2018 Verleur
2018/0343926 A1 12/2018 Wensley
2019/0056131 A1 2/2019 Warren
2019/0098935 A1 4/2019 Phan
2019/0116863 A1 4/2019 Dull
2019/0133186 A1 5/2019 Fraser
2019/0158938 A1 5/2019 Bowen
2019/0166913 A1 6/2019 Trzecieski
2019/0167923 A1 6/2019 Kessler
2019/0216135 A1 7/2019 Guo
2019/0255554 A1 8/2019 Selby
2019/0289914 A1 9/2019 Liu
2019/0289915 A1 9/2019 Heidl
2019/0289918 A1 9/2019 Hon
2019/0321570 A1 10/2019 Rubin
2019/0329281 A1 10/2019 Lin
2019/0335580 A1 10/2019 Lin
2019/0336710 A1 11/2019 Yamada
2019/0037473 A1 12/2019 Chen
2019/0373679 A1 12/2019 Fu
2019/0374730 A1 12/2019 Chen
2019/0387795 A1 12/2019 Fisher
2020/0000143 A1 1/2020 Anderson
2020/0000146 A1 1/2020 Anderson
2020/0009600 A1 1/2020 Tan
2020/0016344 A1 1/2020 Scheck
2020/0022416 A1 1/2020 Alarcon
2020/0046030 A1 2/2020 Krietzman
2020/0068949 A1 3/2020 Rasmussen
2020/0085100 A1 3/2020 Hoffman
2020/0120989 A1 4/2020 Danek
2020/0120991 A1 4/2020 Hatton
2020/0146361 A1 5/2020 Silver
2020/0178598 A1 6/2020 Mitchell
2020/0178606 A1 6/2020 Liu
2020/0214349 A1 7/2020 Liu
2020/0221771 A1 7/2020 Atkins
2020/0221776 A1 7/2020 Liu
2020/0245692 A1 8/2020 Cameron
2020/0345058 A1 11/2020 Bowen
2020/0404975 A1 12/2020 Chen

(56) References Cited

U.S. PATENT DOCUMENTS

| | | | |
|---|---|---|---|
| 2021/0015957 | A1 | 1/2021 | Bush |
| 2021/0076733 | A1 | 3/2021 | Liu |
| 2021/0112858 | A1 | 4/2021 | Liu |
| 2021/0120880 | A1 | 4/2021 | Liu |
| 2021/0153548 | A1 | 5/2021 | Twite |
| 2021/0153549 | A1 | 5/2021 | Twite |
| 2021/0153564 | A1 | 5/2021 | Hourmand |
| 2021/0153565 | A1 | 5/2021 | Twite |
| 2021/0153566 | A1 | 5/2021 | Hourmand |
| 2021/0153567 | A1 | 5/2021 | Twite |
| 2021/0153568 | A1 | 5/2021 | Twite |
| 2021/0153569 | A1 | 5/2021 | Twite |
| 2021/0177056 | A1 | 6/2021 | Yilmaz |
| 2021/0212362 | A1 | 7/2021 | Liu |
| 2021/0378303 | A1 | 12/2021 | Liu |
| 2021/0401061 | A1 | 12/2021 | Davis |
| 2022/0030942 | A1 | 2/2022 | Lord |
| 2022/0151301 | A1 | 5/2022 | Liu |
| 2022/0240589 | A1 | 8/2022 | Liu |
| 2022/0273037 | A1 | 9/2022 | Liu |
| 2022/0279857 | A1 | 9/2022 | Liu |
| 2022/0287361 | A1 | 9/2022 | Kim |
| 2022/0295876 | A1 | 9/2022 | Liu |
| 2022/0395023 | A1 | 12/2022 | Liu |
| 2022/0400747 | A1 | 12/2022 | Liu |
| 2023/0001107 | A1 | 1/2023 | Connolly |
| 2023/0013741 | A1 | 1/2023 | Liu |
| 2023/0020762 | A1 | 1/2023 | Liu |
| 2023/0165303 | A1 | 6/2023 | Liu |
| 2023/0292839 | A1 | 9/2023 | Kim |

FOREIGN PATENT DOCUMENTS

| | | | |
|---|---|---|---|
| CN | 104055225 | A | 9/2014 |
| CN | 104082853 | A | 10/2014 |
| CN | 204070580 | U | 1/2015 |
| CN | 204499481 | U | 7/2015 |
| CN | 105768238 | A | 7/2016 |
| CN | 105795526 | A | 7/2016 |
| CN | 105876873 | A | 8/2016 |
| CN | 205432145 | U | 8/2016 |
| CN | 106108118 | A | 11/2016 |
| CN | 205831074 | A | 12/2016 |
| CN | 106422005 | | 2/2017 |
| CN | 205947130 | U | 2/2017 |
| CN | 206025223 | U | 3/2017 |
| CN | 206043451 | U | 3/2017 |
| CN | 206079025 | U | 4/2017 |
| CN | 206119183 | U | 4/2017 |
| CN | 206119184 | U | 4/2017 |
| CN | 106617319 | A | 5/2017 |
| CN | 206303211 | U | 7/2017 |
| CN | 206333372 | U | 7/2017 |
| CN | 107048479 | A | 8/2017 |
| CN | 206586397 | U | 10/2017 |
| CN | 206949536 | U | 2/2018 |
| CN | 107822195 | | 3/2018 |
| CN | 207185926 | | 4/2018 |
| CN | 105476071 | | 5/2018 |
| CN | 207383536 | | 5/2018 |
| CN | 207400330 | | 5/2018 |
| CN | 108283331 | A | 7/2018 |
| CN | 105747277 | A | 8/2018 |
| CN | 108355210 | A | 8/2018 |
| CN | 105876873 | B | 12/2018 |
| CN | 109619655 | A | 1/2019 |
| CN | 208354603 | | 1/2019 |
| CN | 208434721 | U | 1/2019 |
| CN | 106108118 | B | 4/2019 |
| CN | 208837110 | U | 5/2019 |
| CN | 209060228 | U | 7/2019 |
| CN | 110150760 | A | 8/2019 |
| CN | 209255084 | U | 8/2019 |
| CN | 105876870 | B | 11/2019 |
| CN | 209900345 | U | 1/2020 |
| CN | 210076566 | U | 2/2020 |
| CN | 210225387 | | 3/2020 |
| CN | 110946315 | A | 4/2020 |
| CN | 111229528 | | 6/2020 |
| CN | 111838775 | | 10/2020 |
| CN | 211675730 | U | 10/2020 |
| CN | 212441811 | | 2/2021 |
| CN | 214289213 | | 9/2021 |
| CN | 214483267 | | 10/2021 |
| CN | 215819888 | | 2/2022 |
| CN | 217342045 | | 9/2022 |
| CN | 217609513 | | 10/2022 |
| CN | 217643921 | U | 10/2022 |
| CN | 115336802 | | 11/2022 |
| CN | 217826736 | | 11/2022 |
| CN | 116807059 | | 9/2023 |
| CN | 116850853 | | 10/2023 |
| DE | 2656370 | A1 | 6/1978 |
| DE | 2656370 | B2 | 11/1978 |
| DE | 2656370 | C3 | 7/1979 |
| DE | 100 51 792 | A1 | 5/2002 |
| DE | 10122065 | A1 | 12/2002 |
| EP | 0 258 637 | A1 | 3/1988 |
| EP | 0 295 122 | A2 | 12/1988 |
| EP | 0 258 637 | B1 | 6/1990 |
| EP | 0 442 510 | A1 | 8/1991 |
| EP | 0 516 565 | A1 | 12/1992 |
| EP | 0 442 510 | B1 | 1/1995 |
| EP | 0 516 565 | B1 | 4/1996 |
| EP | 0 824 927 | A | 2/1998 |
| EP | 0 833 695 | A1 | 4/1998 |
| EP | 0 845 220 | A1 | 6/1998 |
| EP | 0 893 071 | A1 | 1/1999 |
| EP | 0 970 627 | A1 | 1/2000 |
| EP | 1 083 952 | B1 | 12/2005 |
| EP | 1 618 803 | A1 | 1/2006 |
| EP | 1 618 803 | B1 | 12/2008 |
| EP | 3 088 007 | A1 | 11/2016 |
| EP | 3 192 381 | A1 | 7/2017 |
| EP | 3 278 678 | A1 | 2/2018 |
| EP | 3 298 912 | A1 | 3/2018 |
| EP | 3 088 007 | B1 | 11/2018 |
| EP | 3 434 118 | A1 | 1/2019 |
| EP | 3 469 927 | A1 | 4/2019 |
| EP | 3 505 098 | | 7/2019 |
| EP | 3 520 634 | A1 | 8/2019 |
| EP | 3 278 678 | B1 | 10/2019 |
| EP | 3 545 778 | A1 | 10/2019 |
| EP | 3 574 902 | A1 | 12/2019 |
| EP | 3 516 971 | | 3/2021 |
| EP | 3 528 651 | | 5/2021 |
| EP | 3 837 999 | A1 | 6/2021 |
| EP | 3 574 778 | | 7/2021 |
| EP | 3 593 656 | | 10/2021 |
| EP | 4252561 | | 10/2023 |
| EP | 4033927 | | 11/2023 |
| FR | 3043576 | A1 | 5/2017 |
| FR | 3064502 | A1 | 10/2018 |
| GB | 1 528 391 | A | 10/1978 |
| GB | 2566766 | A | 3/2019 |
| GB | 2570439 | A | 7/2019 |
| JP | 05093575 | U | 12/1993 |
| JP | 2579614 | Y2 | 8/1998 |
| JP | 2001069963 | A | 3/2001 |
| JP | 2005288400 | A | 10/2005 |
| JP | 2008-104966 | A | 5/2008 |
| JP | 2011-500160 | | 1/2011 |
| JP | 2012-507208 | | 3/2012 |
| JP | 2014-004042 | | 1/2014 |
| JP | 2019515684 | | 6/2019 |
| JP | 2019521671 | A | 8/2019 |
| JP | 2019-524113 | | 9/2019 |
| JP | 2019-526240 | | 9/2019 |
| JP | 2019-526241 | | 9/2019 |
| JP | 2020535846 | A | 12/2020 |
| JP | 2022032444 | | 2/2022 |
| KR | 20120107219 | A | 10/2012 |
| KR | 210-2013-0052119 | | 5/2013 |
| KR | 10-2013-0095024 | | 8/2013 |

(56) References Cited

FOREIGN PATENT DOCUMENTS

| | | | |
|---|---|---|---|
| KR | 20230024816 | | 2/2023 |
| KR | 20230115452 | | 8/2023 |
| KR | 20230123537 | | 8/2023 |
| KR | 102584559 | | 10/2023 |
| KR | 102587103 | | 10/2023 |
| WO | WO 92/21332 | A1 | 12/1992 |
| WO | WO 93/09881 | A2 | 5/1993 |
| WO | WO 2000/050111 | A | 8/2000 |
| WO | WO 02094342 | A2 | 11/2002 |
| WO | WO 2002/055131 | A2 | 1/2003 |
| WO | WO 2003/055486 | A | 7/2003 |
| WO | WO 2003/0101454 | A | 12/2003 |
| WO | WO 2004/080216 | | 9/2004 |
| WO | WO 2007/083088 | A1 | 7/2007 |
| WO | WO 2008/076717 | A1 | 6/2008 |
| WO | WO 2009/096346 | A1 | 8/2009 |
| WO | WO 2012/062600 | A1 | 5/2012 |
| WO | WO 2012/138835 | A2 | 10/2012 |
| WO | WO 2013/028934 | A1 | 2/2013 |
| WO | WO 2014/182736 | A1 | 11/2014 |
| WO | WO2015/084544 | A1 | 6/2015 |
| WO | WO 2015/115006 | A1 | 8/2015 |
| WO | WO 2015/128499 | A1 | 9/2015 |
| WO | WO 2016/010864 | A1 | 1/2016 |
| WO | WO 2016/116386 | | 7/2016 |
| WO | WO 2016/118941 | A1 | 7/2016 |
| WO | WO 2016/175720 | A1 | 11/2016 |
| WO | WO 2016/196915 | A1 | 12/2016 |
| WO | WO 2017/076590 | A1 | 5/2017 |
| WO | WO 2017/108268 | A1 | 6/2017 |
| WO | WO 2017/143515 | A1 | 8/2017 |
| WO | WO 2017/177159 | A3 | 10/2017 |
| WO | WO 2017/197704 | A1 | 11/2017 |
| WO | WO 2017/205692 | | 11/2017 |
| WO | WO 2017/206022 | A1 | 12/2017 |
| WO | WO 2017/206212 | A1 | 12/2017 |
| WO | WO 2017/215221 | A1 | 12/2017 |
| WO | WO 2018/000761 | A1 | 1/2018 |
| WO | WO 2018/000829 | A1 | 1/2018 |
| WO | WO 2018/023920 | A1 | 2/2018 |
| WO | WO2018/027189 | A2 | 2/2018 |
| WO | WO 2018/032672 | A1 | 2/2018 |
| WO | WO 2018/040380 | A1 | 3/2018 |
| WO | WO 2018/041106 | A1 | 3/2018 |
| WO | WO 2018/058884 | A1 | 4/2018 |
| WO | WO 2018/111843 | | 6/2018 |
| WO | WO 2018/113669 | A1 | 6/2018 |
| WO | WO 2018/115781 | A1 | 6/2018 |
| WO | WO 2018/163366 | A1 | 9/2018 |
| WO | WO 2018/167066 | | 9/2018 |
| WO | WO 2018/188616 | A1 | 10/2018 |
| WO | WO 2018/188638 | A1 | 10/2018 |
| WO | WO 2018/211252 | A1 | 11/2018 |
| WO | WO 2018/220586 | A2 | 12/2018 |
| WO | WO2018/220599 | A1 | 12/2018 |
| WO | WO 2019/016681 | | 1/2019 |
| WO | WO 2019/048749 | A1 | 3/2019 |
| WO | WO 2019/052506 | A1 | 3/2019 |
| WO | WO 2019/052574 | A1 | 3/2019 |
| WO | WO 2019/069160 | A1 | 4/2019 |
| WO | WO 2019/138076 | A1 | 7/2019 |
| WO | WO 2019/173923 | | 9/2019 |
| WO | WO 2019/198688 | | 10/2019 |
| WO | WO 2019/211324 | | 11/2019 |
| WO | WO 2019/238064 | | 12/2019 |
| WO | WO 2019/242746 | A1 | 12/2019 |
| WO | WO 2020/019030 | A1 | 1/2020 |
| WO | WO 2020/048437 | A1 | 3/2020 |
| WO | WO 2020/057636 | A2 | 3/2020 |
| WO | WO2020187138 | A1 | 9/2020 |
| WO | WO 2020/225534 | A1 | 11/2020 |
| WO | WO 2021/036827 | A1 | 3/2021 |
| WO | WO2022/104246 | | 5/2022 |
| WO | WO2022/200151 | | 9/2022 |
| WO | WO2022/203187 | | 9/2022 |
| WO | WO 2023/018059 | | 2/2023 |
| WO | WO2023/143058 | | 8/2023 |
| WO | WO2023/179691 | | 9/2023 |
| WO | WO2023/249371 | | 12/2023 |

OTHER PUBLICATIONS

UKIPO Search Report dated Nov. 24, 2021 for Application No. GB2111261.0.

UKIPO Search Report dated Nov. 24, 2021 for Application No. GB2113658.5.

UKIPO Search Report dated Nov. 24, 2021 for Application No. GB2113623.9.

ISR and Written Opinion for International Appl. No. PCT/GB2021/050842 mailed Jul. 5, 2021.

UKIPO Search Report for UK Appl. No. GB2104872.3 dated Jun. 25, 2021.

EPO Search Report and Search Opinion for International Appl. No. PCT/IB2019/060812 dated Jun. 22, 2021.

ISR and Written Opinion for International Appl. No. PCT/GB2021/050817 mailed Jun. 17, 2021.

Extended European Search Report and Search Opinion for corresponding EP Appl. No. 20214228.7 dated May 26, 2021.

ISR for corresponding PCT Application No. PCT/GB2020/053219 mailed Mar. 31, 2021.

Written Opinion mailed Nov. 10, 2020 for corresponding International Application No. PCT/IB2019/060812.

ISR mailed Nov. 10, 2020 for corresponding International Application No. PCT/IB2019/060812.

EPO Search Report mailed Nov. 9, 2020 for corresponding EPO Application No. 19870059.3 (PCT/IB2019/060808).

Written Opinion mailed Nov. 4, 2020 for corresponding International Application No. PCT/IB2019/060806.

ISR mailed Nov. 4, 2020 for corresponding International Application No. PCT/IB2019/060806.

Written Opinion mailed Nov. 4, 2020 for corresponding International Application No. PCT/IB2019/060807.

ISR mailed Nov. 4, 2020 for corresponding International Application No. PCT/IB2019/060807.

Written Opinion mailed Oct. 20, 2020 for corresponding International Application No. PCT/IB2019/060811.

ISR mailed Oct. 20, 2020 for corresponding International Application No. PCT/IB2019/060811.

Written Opinion mailed Oct. 19, 2020 for corresponding International Application No. PCT/IB2019/060810.

ISR mailed Oct. 19, 2020 for corresponding International Application No. PCT/IB2019/060810.

EPO Search Report dated Sep. 16, 2020 for corresponding EPO Application No. 20168231.

Extended EPO Search Report mailed Sep. 15, 2020 for corresponding EPO Application No. 20168938.7

Written Opinion mailed Jun. 25, 2020 for corresponding International Application No. PCT/IB2019/060808.

ISR mailed Jun. 25, 2020 for corresponding International Application No. PCT/IB2019/060808.

Written Opinion mailed Apr. 29, 2020 for corresponding International Application No. PCT/IB2019/055192.

ISR mailed Apr. 29, 2020 for corresponding International Application No. PCT/IB2019/055192.

EPO Supplementary Search Report for EPO Application No. EP 3 278 678 A4 dated Oct. 4, 2018.

International Search Report for International Appl. No. WO 2017/177159 A3 mailed Sep. 26, 2017.

EPO search report dated Sep. 20, 2017 for corresponding EPO Application No. 20168245.7.

EPO Supplementary Search Report for EPO Application No. EP 1 618 803 A4 dated Jul. 27, 2007.

EPO Search Report dated Oct. 27, 2021 for corresponding European Application No. 19870058.5.

EPO Search Report dated Nov. 12, 2021 for corresponding European Application No. 19870060.1.

(56) References Cited

OTHER PUBLICATIONS

ISR and Written Opinion mailed Mar. 10, 2022 for Intl Appl. No. PCT/GB2021053312.
ISR and Written Opinion mailed Mar. 10, 2022 for Intl Appl. No. PCT/GB2021053311.
ISR and Written Opinion mailed Mar. 10, 2022 for Intl Appl. No. PCT/GB2021053316.
ISR and Written Opinion mailed Oct. 20, 2020 for Intl Appl. No. PCT/IB2019/060809.
Akira Kubo, Part 1: What is Personal Authentication?—The Last Resort for Internet Security-Series: Re-Introduction to PKI, Japan, @IT, Apr. 5, 2003; https://atmarkit.itmedia.co.jp/fsecurity/rensai/re_pki01/re_pki01.html (newly cited reference showing well-known technique) (No English version).

* cited by examiner

PERSONAL ULTRASONIC ATOMIZER DEVICE ABLE TO CONTROL THE AMOUNT OF LIQUID FLOW

CROSS-REFERENCE TO RELATED APPLICATIONS

This application is a National Phase Application under 35 U.S.C. § 371 of PCT/IB2019/055192, filed Jun. 20, 2019 (published on Dec. 24, 2020 as WO 2020/254862 A1) the entire contents of which are incorporated herein by reference.

FIELD OF THE INVENTION

The invention relates to an ultrasonic atomizer device for personal use, and more particularly to an atomizer device for atomizing a liquid using ultrasonic oscillation of piezoelectric materials.

BACKGROUND OF THE INVENTION

The harmful effects of smoking and tobacco products have been known for many years, and while a prevalent cause of disease and even death, most tobacco products continue to be sold and used worldwide.

Deemed a 'safer' alternative to smoking and smoking products, electronic smoking devices have been developed. The electronic devices use heating coils to convert a nicotine-based liquid to a fine mist or vape. The vape is then inhaled by the user in a similar fashion to smoking a cigarette. These devices have however, failed to eliminate all harmful components from the aerosol. Therefore, the correct terminology for such devices is 'reduced' risk products.

Increasingly studies have shown that the harmful side-effects of smoking, including heart, lung and mouth cancer, can be related to the combustion of the tobacco products, such as dry tobacco or nicotine-based liquids, using heat and/or an open flame. During this process the chemical nature of the compounds are changed, and it is this change which has been closely associated with the carcinogenic effects of smoking. Further, burning nicotine based-liquids, liquids or E-liquids as they are known, produces formaldehyde and acrolein. These are compounds which are known to be toxins to the body.

To avoid combustion, and the chemical change which takes place as a result, devices utilizing liquid cavitation have replaced heating and/or combustion. Oscillation of piezoelectric materials is used to cavitate nicotine-based liquids placed in contact therewith. The cavitation has the same effect of generating a mist or vape, similar to that of the combustible method but without the harmful chemical change in the compounds.

While devices utilizing this cavitation method have begun entering the market place, such devices still suffer from problems, making their introduction to, and uptake by, users undesirable. The devices which are entering the market are prone to leaking, function only in a particular orientation and have little or no external control. Such as control through other electronic devices.

The lack of connectivity of the devices lacks the control needed to monitor nicotine consumption. Thus the devices cannot be used as medical smoke cessation devices.

OBJECT OF THE INVENTION

It is an object of the current invention to address these problems, at least partly, and provide an electronic smoking device which does not use combustion or heat to generate a vape, and which is leak-proof, usable in any orientation, including leak-proof use while inverted, and which may be controllable, remotely, through connection with an electronic device. The controllable nature making the device a candidate for medical smoke cessation.

SUMMARY OF THE INVENTION

In accordance with the invention there is provided a personal ultrasonic atomizer device, which includes a cartridge having a reservoir for holding a liquid to be atomized; a sonication chamber, placed in fluid communication with the reservoir, and a member for controlling the amount of liquid flow into the sonication chamber; where, the reservoir includes a first opening for providing air passage from the surroundings to the interior of the reservoir and a first aperture for providing a flow path from the interior of the reservoir to the sonication chamber; and where the member is engaged with the cartridge to be movable between a sealed position, at which the opening is sealed, and a flow position, at which the opening is open; wherein liquid held in the reservoir is discharged to the sonication chamber once the member is in the flow position and liquid held in the reservoir remains in the reservoir when the member is in the sealed position.

The member may have at least a first slot for providing passage from the surroundings through the member; further where the slot may be aligned with the opening when the member is in the flow position; further still where the slot may be misaligned relative to the opening when the member is in the sealed position; even further still where the sealed position may provide a substantially air-tight seal. The sonication chamber may include an ultrasonic oscillation component and a wick for directing liquid, to be atomized, from the sonication chamber to the component.

The component may include a piezoelectric ceramic piece, a flexible sleeve, to receive the ceramic piece, and an electronic arrangement for driving oscillation of the ceramic piece; further the electronic arrangement may be connected to an energy storage arrangement for driving the oscillation of the ceramic piece.

The wick may be a capillary structure; further the wick may be formed of a sintered metallic material; further still the wick may have an absorbent structure, even further still the material may be cotton.

The reservoir and the sonication chamber may be engageable with one another; further the sonication chamber may include a seat arrangement for receiving the reservoir.

The first aperture may include valve arrangement, biased to a closed position, to seal the aperture and restrict the flow path; further the sonication chamber may include a piston for abutting the valve when the sonication chamber and cartridge are brought together; further still where the piston may overcome the bias of the valve when placed in abutment to move the valve and open the aperture to restore the flow path.

The invention provides further that liquid held in the reservoir will pass through the flow path to the sonication chamber when the member is moved to the open position and when the piston is in abutment with the valve.

The member may be movable between the sealed and flow position and relative to the cartridge in a twist fashion.

In accordance with a further embodiment of the invention, there may be provided a liquid retention means positioned between the member and the reservoir to cover at least the first opening.

The means may be impervious to liquids; further the means may be pervious to air flow.

The means may limit the flow of liquid from the reservoir past the first opening; further the means may limit the flow of liquid from the reservoir through the member when the member is in, or between, the sealed position and/or the flow position. The means may be formed of a foam material; further the means may be formed of any material which is impervious to liquids and which is pervious to air; further the means may be formed of a microporous membrane.

The cartridge and the sonication chamber may include complimentary arrangements for engaging with one another; further such complimentary arrangements may include; a bayonet type arrangement; a threadedly engaged type arrangement; a magnetic arrangement; and, a friction fit arrangement; wherein the seat of the sonication chamber includes a portion of the arrangement and the cartridge includes the complimentary portion of the arrangement.

The invention provides for the cartridge to be dis-engageable from the sonication chamber prior to complete discharge of the liquid in the reservoir; further the cartridge may be re-engageable with the sonication chamber through any one of the complimentary arrangements.

The sonication chamber may be engageable with any number of cartridges in accordance with the invention; further the reservoirs may or may not be completely or partially discharged.

The sonication chamber may include an air inlet port, for introducing air to the sonication chamber from the surroundings; further the air inlet port may be formed to orientate air introduced to the sonication chamber with a flow of atomized liquid exiting the sonication chamber; further still the air inlet port may be in the form of an elongate tubular body having a sidewall extending between opposing ends and having a portion removed from the tube sidewall.

The invention provides further for a channel which includes a first end received in the sonication chamber, and a second end formed as a mouth piece.

The channel may include a cylindrical body, having a proximal end, positioned toward the sonication chamber, and a distal end positioned toward the mouth piece for altering the flow rate of a fluid passing through the channel; further the cylindrical body may narrow from the proximal end to the distal end.

The mouth piece and the member may be the same structure.

In accordance with a further embodiment of the invention there may be provided an electronic system for operating the device; further where the system comprises a computer, an energy storage arrangement, a means for communicating with an electronic device and a Global Positioning System (GPS) module.

The computer may include a contact panel for receiving, and for providing communication with, a microchip; further the computer may operate the device based on the communication with the microchip.

The means for communicating with an electronic device may include wireless communication circuitry, a Bluetooth connectivity circuit, Global System for Mobile Communication (GSM) communication circuitry and placing the device in physical communication with the electronic device; further the means for communicating may communicate with a program provided on the electronic device.

The operation of the device may include the computer preventing or permitting power from the energy storage arrangement to the device; further the computer may operate the device according to the physical location of the device; further still where the physical location of the device may be provided by the Global Positioning System (GPS) module; even further still where the location of the device relative to predetermined geolocation areas may be communicated to the computer.

The cartridge may include a microchip for storing data specific to the reservoir; further the microchip may contact the contact panel during engagement of the cartridge to the sonication chamber.

The data stored on the microchip may include one or more of the following; the make, model and volume of the reservoir and the nature of the liquid held in the reservoir.

BRIEF DESCRIPTION OF THE DRAWINGS

These and other features of the invention will become more apparent by the following description of the embodiment, which is made by way of example, with reference to the accompanying drawings in which.

BRIEF DESCRIPTION OF THE PREFERRED EMBODIMENTS

Figure 1:
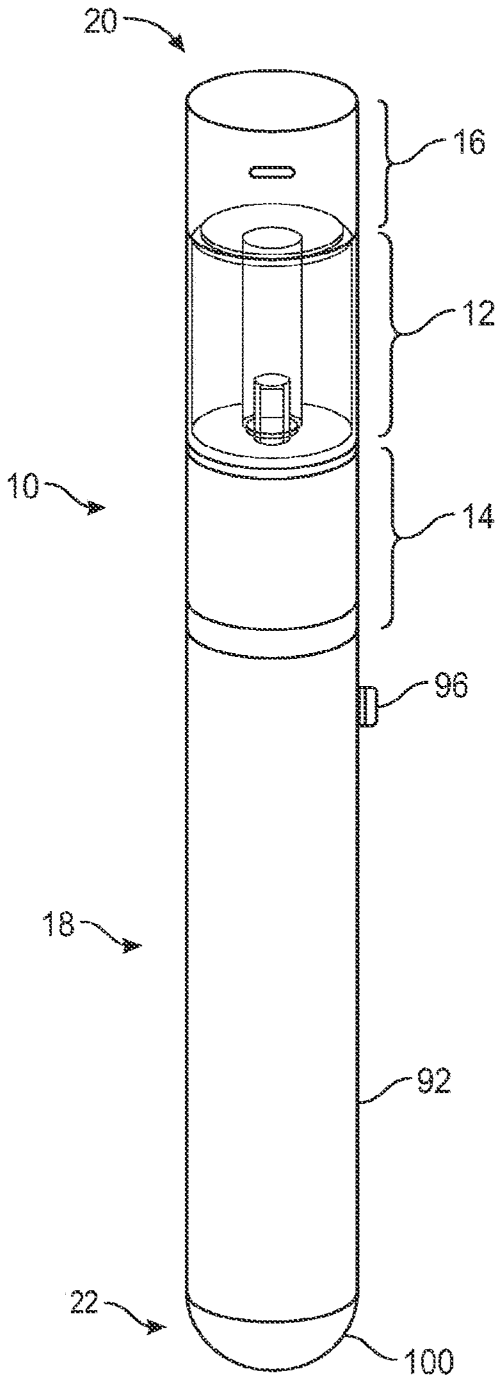
FIG. 1: shows a personal ultrasonic atomizer device in perspective view, in accordance with the invention.

In accordance with the invention there is provided a personal ultrasonic atomizer device 10 as shown in FIG. 1.

The personal ultrasonic atomizer device 10 includes a cartridge 12 for holding a liquid to be atomized, a sonication chamber 14 and a member 16 for controlling the amount of liquid flow to the sonication chamber 14. The cartridge 12, chamber 14 and member 16 are interconnected in sequential fashion, with the cartridge 12 flanked on either side by the sonication chamber 14 and the member 16.

The personal ultrasonic atomizer device 10 includes a casing 18 for housing components used to power and operate the personal ultrasonic atomizer device 10.

The personal ultrasonic atomizer device 10 is shown as an elongate tubular body which includes an end 20, an opposing end 22 and a sidewall 24 which partially extends between the first and second ends 20 and 22.

Figure 2:
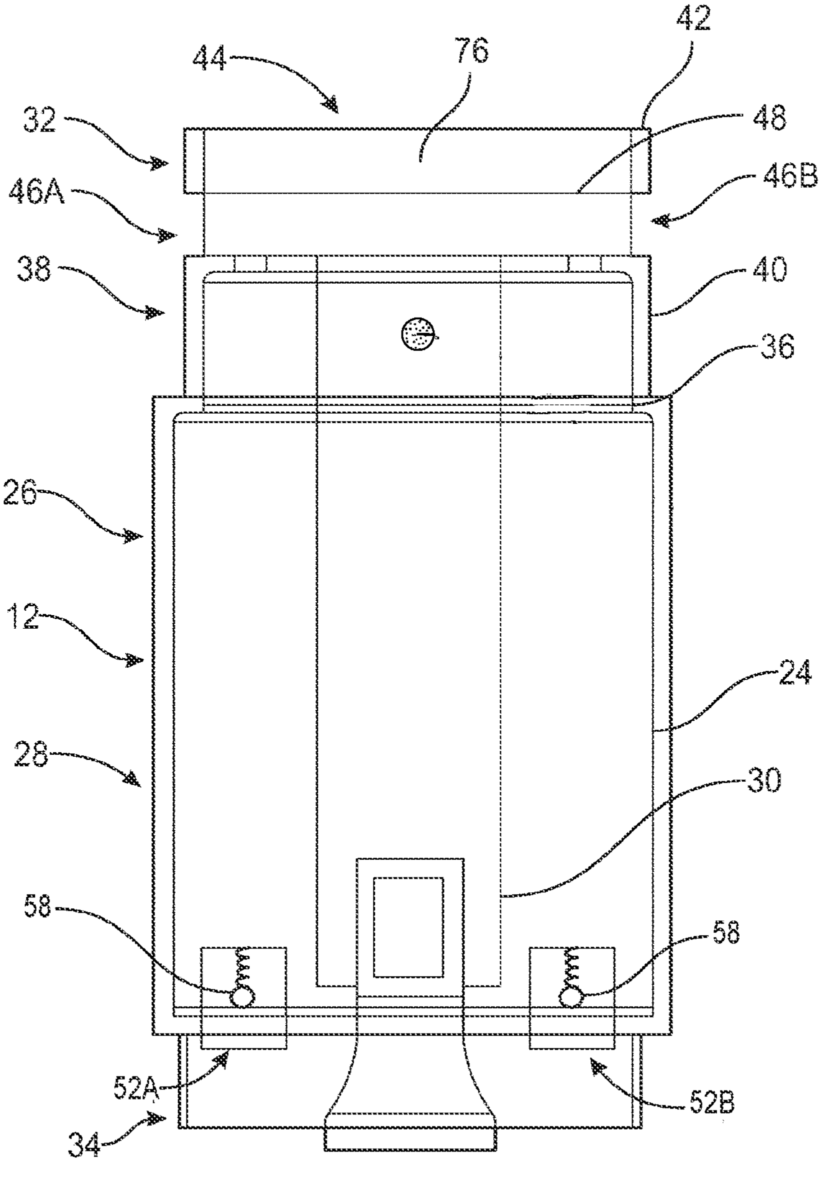
FIG. 2: shows a view from a side and in cross-section of the cartridge in accordance with the invention.

FIG. 2 shows the cartridge 12 which includes a reservoir 26 for holding the liquid to be atomized. In the embodiment shown, the cartridge 12 is an elongate circular shaped body 28 having an internal bore 30, which extends between a first end 32 and an opposed second end 34 of the body 28.

The body 28 includes a shoulder 36, at which the diameter of the body 28 is reduced to form a portion 38. The portion 38 includes a sidewall 40 which extends away from the first end 32 to terminate in a circular ridge 42. A recess 44 is formed in the space between the sidewall 40 and the circular ridge 42.

The sidewall 40 includes a first duct 46A and a diametrically opposed second duct 46B, which both extend through the sidewall 40. Additionally, a guide formation 48, extends laterally from the sidewall 40.

The portion 38 provides a mating arrangement for connecting the member 16.

Figure 3A:
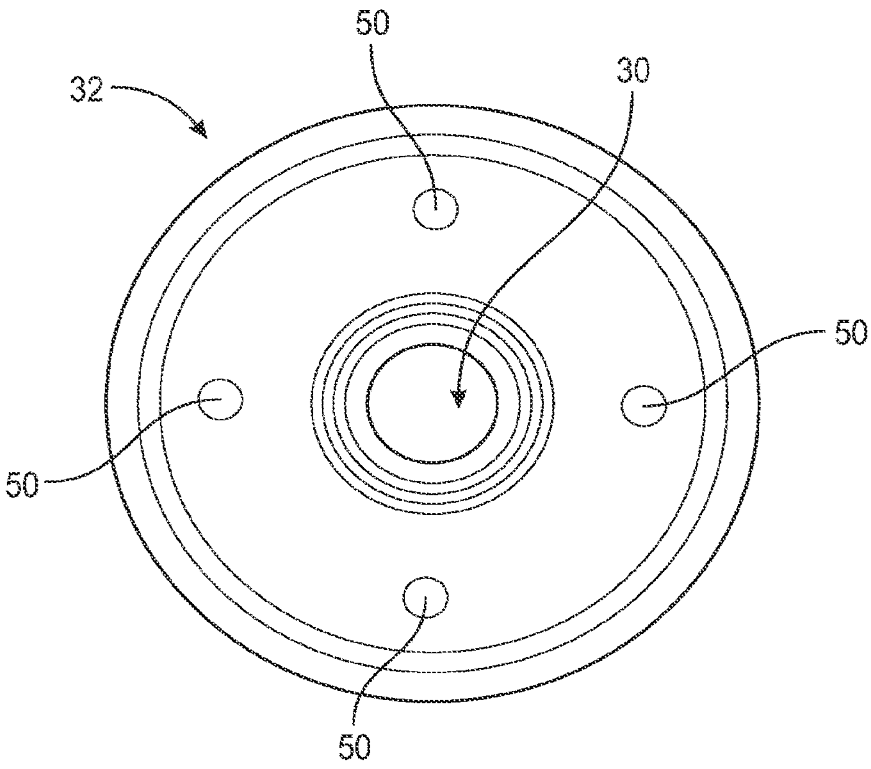
FIG. 3: shows end views of the cartridge of FIG. 2.

The cartridge 12 additionally includes at least a first opening 50, located along the first end 32 and at least a first aperture 52A located along the second end 34. This is more clearly shown in FIGS. 3A and 3B, respectively.

Situated along the second end 34 may be one or more metal plates 110 and a microchip 126. The metal plates 110 form part of a complimentary arrangement for engaging the cartridge 12 with the sonication chamber 14 and will be dealt with in further detail below. Likewise, the microchip 126 will also be discussed in greater detail below.

Opening 50 provides a passageway from the surroundings to the reservoir 26. In the current embodiment the cartridge 12 includes four such openings, all of which provide a passageway from the surroundings to the reservoir 26.

Figure 3B:
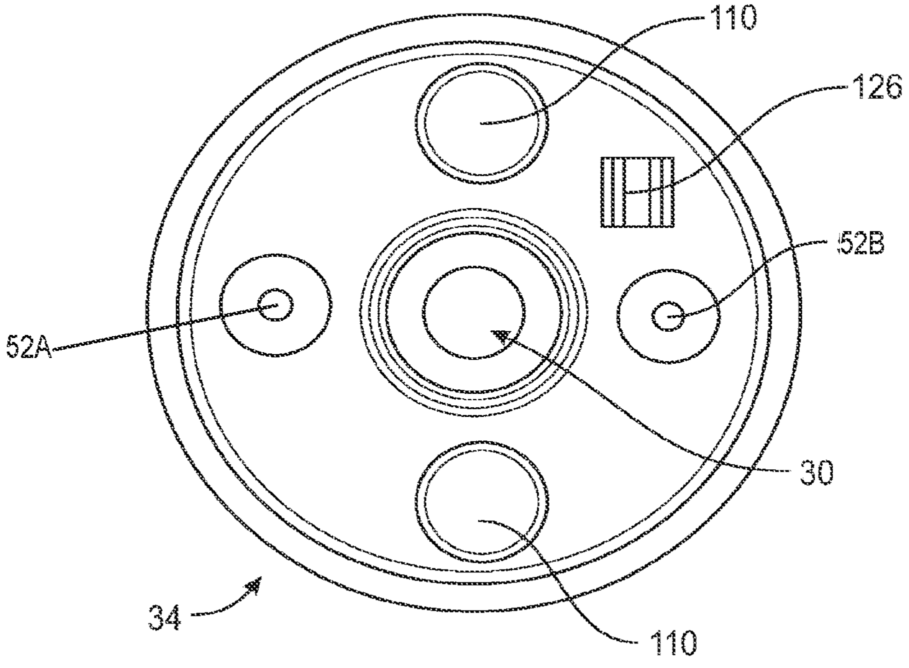

The at least first aperture 52A, provides a flow path 54 from the reservoir 26 out of the cartridge 12. As is shown in FIG. 3B. A second aperture 52B is also present. The invention is not deemed to be limited as to the number of apertures in this respect.

Figure 4:
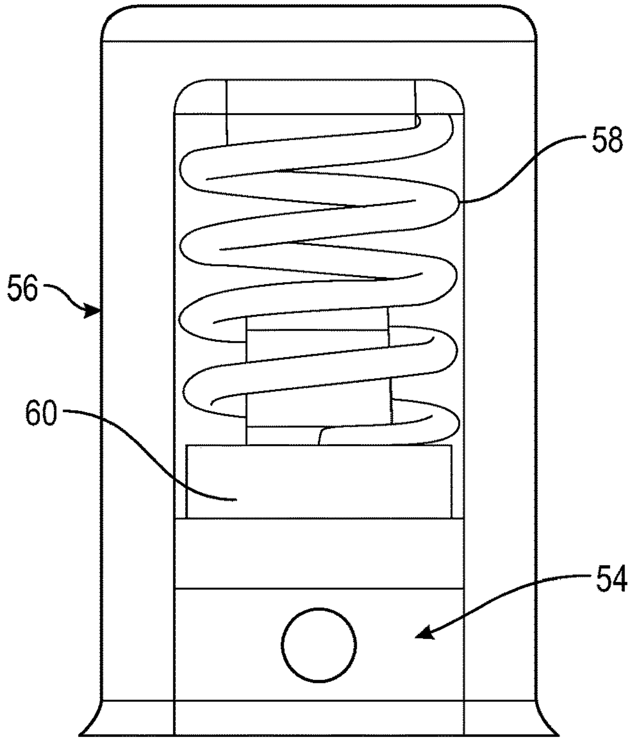
FIG. 4: shows an enlarged view, in cross-section, of a valve arrangement in accordance with the invention.

Apertures 52A and 52B each include a valve arrangement 56. An enlarged view of the valve arrangement 56 is shown in FIG. 4. The arrangement includes a biasing means 58, such as a mechanical spring, and a stopper 60 for sealing the apertures 52A and 52B, when biased toward the sealing position. The flow path 54 will be restricted when the stopper is in the sealing position.

Figure 5:
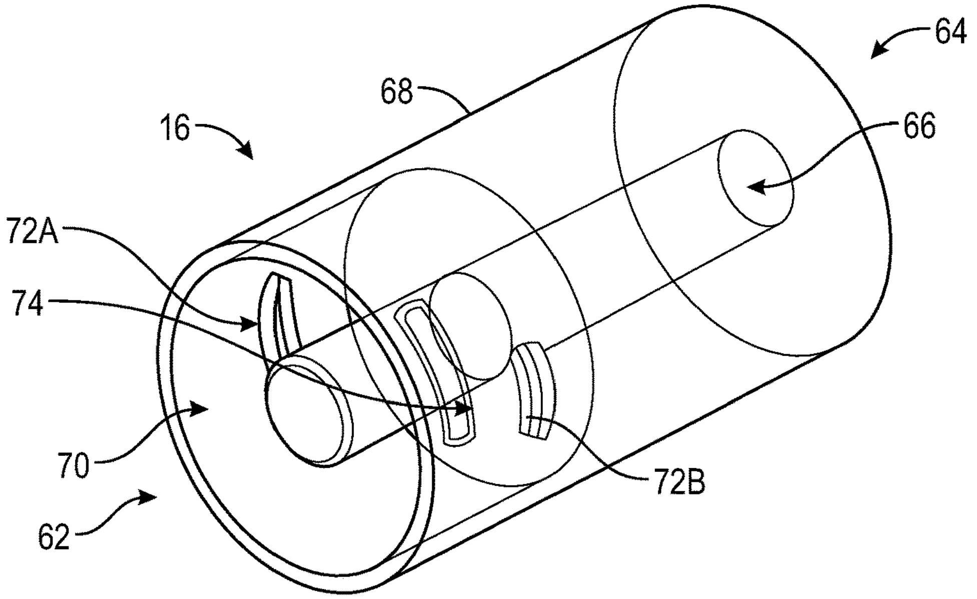
FIG. 5: shows a view in perspective of a member in accordance with the invention.

Turning to FIG. 5 which shows the member 16. The member 16 is formed as an elongate circular body and includes a leading end 62, a trailing end 64, an internal orifice 66, which extends between the leading end 62 and trailing end 64, and an outerwall 68 which extends between the two ends 62 and 64.

Positioned toward the leading end 62 is an internal step 70, which step is compatible to receive portion 38 of the cartridge 12. The internal step 70 additionally includes a pair of opposing slots 72A and 72B respectively, and at least one groove 74, for receiving the guide formation 48.

The member 16 is connected to the cartridge 12, by portion 38 being received by internal step 70. The cartridge 12 is inserted into the member 16 until shoulder 36 abuts the leading end 62 of the member 16, and the guide formation 48 is received within the groove 74.

Once connected, the member 16 is movable relative to the cartridge 12. The movement may be in the form of a twist, as shown in the Figures, where the degree of movement will be limited, to an extent, by the movement of the guide formation 48 as it travels through groove 74.

Twisting the member 16 relative to the cartridge 12 results in slots 72A and 72B becoming aligned, or misaligned, with the ducts 46A and 46B, respectively. Alignment of the slots 72A and 72B with the ducts 46A and 46B will provide a passageway for air from the surroundings to the recess 44, and hence, to openings 50. This alignment relates to a flow position.

The degree of twisting movement of the member 16 relative to the cartridge 12, is limited to the degree of movement of the guide formation 48 as it travels through groove 74. This movement may also correlate to the alignment or misalignment of the slots 72A and 72B with the ducts 46A and 46B. Mis-alignment relates to a sealing position.

The member 16, once connected to the cartridge 12, and twisted such that the slots 72A and 72B are misaligned with the ducts 46A and 46B, provides a substantially air-tight seal.

While the twisting of the member 16, relative to the cartridge 12, is described to align the slots 72A and 72B with the ducts 46A and 46B, it is clear that any movement of the member 16 in which the alignment takes place may be incorporated in terms of the current description. The invention is not deemed to be limited in this respect. Further the member 16 may be connected to the cartridge 12 in any fashion, wherein movement, relative to the cartridge, will result in the member aligning or misaligning the slots 72A and 72B with the ducts 46A and 46B. The connection may include vertical, or lateral movement of the member.

Located within the recess 44 is a ring-shaped liquid retention means 76. The liquid retention means 76, once inserted into the recess 44 will cover the slots 72A and 72B of the member 16. The liquid retention means 76 will further cover the openings 50 of the cartridge 12. The liquid retention means 76 is substantially pervious to air but, is substantially impervious to a liquid.

When in use, the liquid retention means 76 will provide a buffer between the surroundings and the openings 50. Liquid held in the reservoir 26 which may pass through the openings 50 will be retained by the liquid retention means 76, and hence is prevented from passing through the ducts 46A and 46B, and/or, slots 72A and 72B.

The liquid retention means 76 provides an anti-leak guard, which limits movement of the liquid from the reservoir 26 and pass the openings 50. Placing the cartridge 12 and/or reservoir 26 in any orientation will have little or no effect on the anti-leak properties.

The liquid retention means 76 provides for the personal ultrasonic atomizer device 10 to be used in any orientation, without the liquid being leaked out of the reservoir 26 and/or the personal ultrasonic atomizer device 10 itself.

This is particularly useful where a user of the device may be horizontal (i.e. lying down). The personal ultrasonic atomizer device 10 may be used in the horizontal position without any leakage of liquid.

The flow of air through the liquid retention means 76 will not be restricted, to a degree. As such air from the surroundings may flow through the liquid retention means 76, through the openings 50 and to reservoir 26. This will be the position when the member 16 is twisted to align the slots 72A and 72B with the ducts 46A and 46B.

The flow of air will be limited, substantially, when the member 16 is twisted to misalign the slots 72A and 72B and ducts 46A and 46B. Once misaligned the member 16 and cartridge 12 will provide a substantial air-tight seal between them, thus limiting liquid and air-flow from the surroundings to the reservoir 26.

A vacuum within the reservoir 26 is formed when the cartridge 12 and the member 16 are connected to one another, and the member 16 is set to the sealing position. The vacuum prevents the liquid held in the reservoir 26, from flowing through the openings 50 (this is true even when the valve arrangement 56 is in a flow position).

To release the vacuum, air from the surroundings must be introduced to the reservoir 26. This is possible by moving the member 16 from the sealing potion to the flow position. Air may then flow through the slots 72A and 72B and the ducts 46A and 46B through the openings 50 to the reservoir 26. By releasing the vacuum, liquid in the reservoir 26 may flow out of the apertures 52A and 52B.

The vacuum may be reinstated by moving the member 16 to the sealing position and restricting the air flow.

The rate at which liquid flows from the reservoir 26 through the apertures 52A and 52B may also be controlled, to a degree, by the amount of air being introduced. Controlling the air flow is possible by the limiting the degree to which the slots 72A and 72B and ducts 46A and 46B are aligned and/or misaligned, through the movement of the member 16 relative to the cartridge 12.

Figure 6:
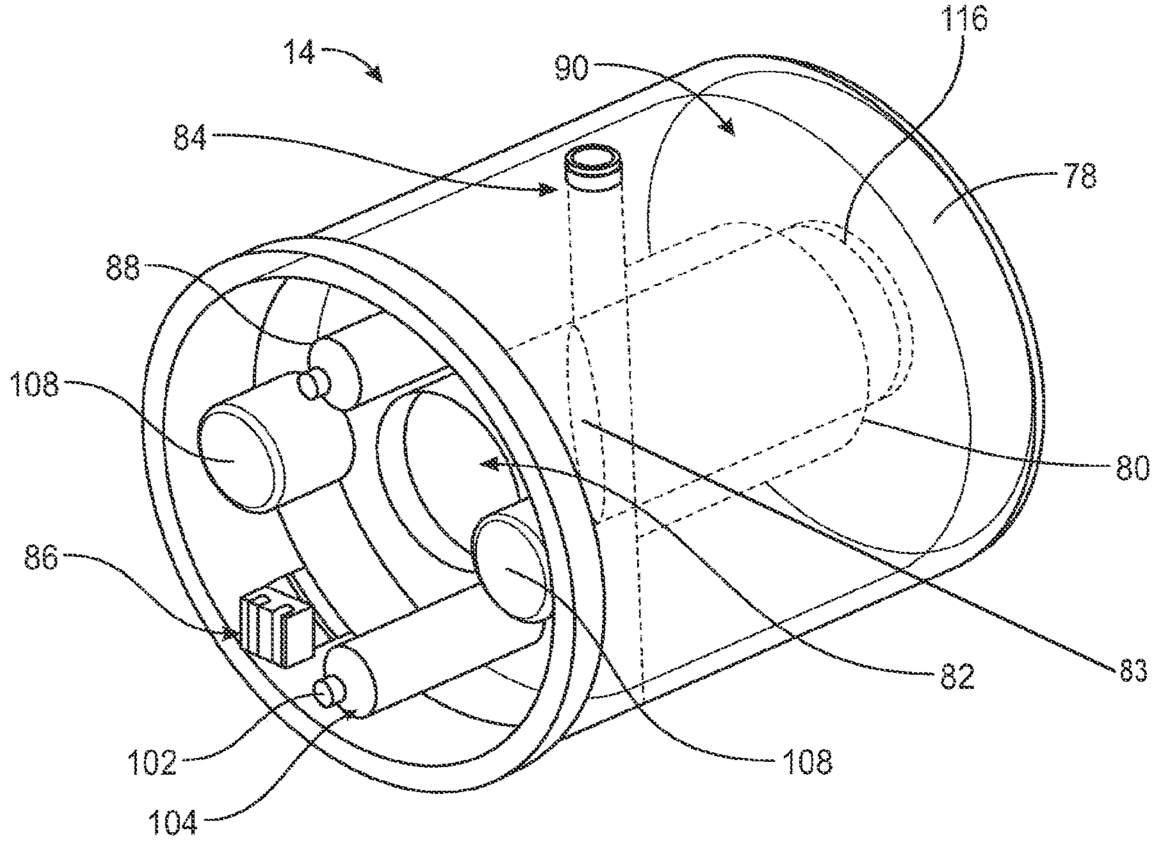
FIG. 6: shows a perspective view, in partial cross-section, of a sonication chamber in accordance with the invention.

Turning to FIG. 6, which shows the sonication chamber 14. The sonication chamber 14 includes the ultrasonic oscillation arrangement 78, provided for atomizing a liquid. The sonication chamber 14 further includes a wick 80, a portion of an inhalation channel 82, an air inlet port 84, a contact panel 86, a rigid connector 88 and an inner chamber 90. The inhalation channel 82 is preferably an elongate tubular body having a sidewall extending between opposing ends having a portion 83 removed from the tube sidewall.

Casing 18 houses a portion of the sonication chamber 14 and includes an outer shell 92, conterminous with the outerwall 24 of the cartridge 12 and the sidewall 68 of the member 16.

The casing 18 houses additional components for powering and operating the personal ultrasonic atomizer device 10.

Figure 8:
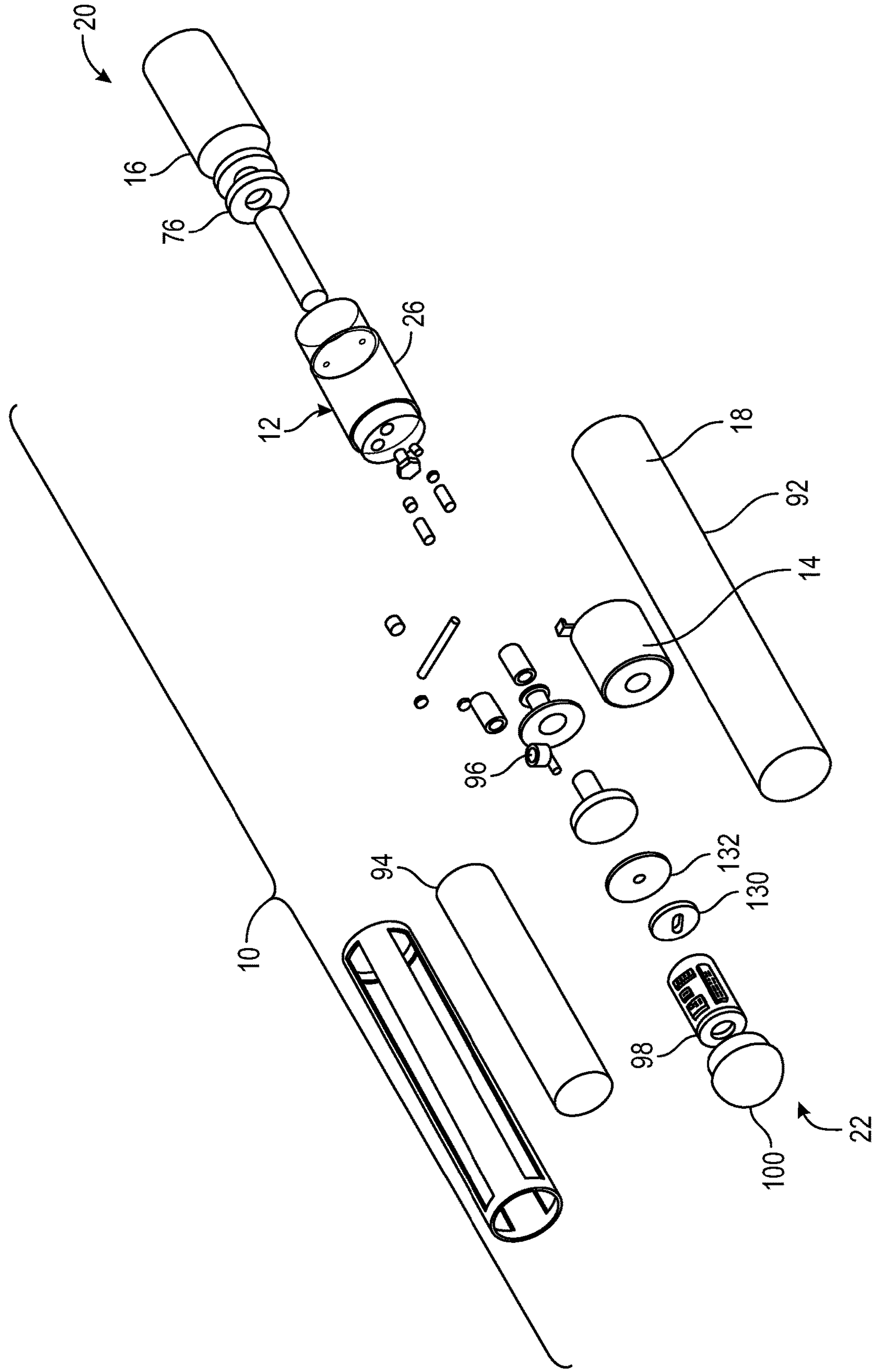
FIG. 8: shows the personal ultrasonic atomizer device in accordance with the invention in an exploded view; and, FIG. 9: shows a flow diagram depicting the operation of the device in accordance with the invention.

These components include an energy storage arrangement 94, activation switch 96, computer 98 and a visual indicator 100, such as a light emitting diode, for providing signals to a user. These are more clearly shown in the exploded view of the personal ultrasonic atomizer device 10 in FIG. 8.

The sonication chamber 14 includes two rigid connectors 88. Each of the rigid connectors 88 include a rigid piston 102 and a hole 104 and fulfil two roles in the invention. The first of these roles is to provide a liquid path 106 for a liquid from outside of the sonication chamber 14, through the hole 104 to an inner chamber 90, housed within the sonication chamber 14. A liquid to be atomized is held in the inner chamber 90 before atomization takes place. The inner chamber 90 places the liquid in fluid communication with the wick 80.

The second role of the connectors is to move the stoppers 60 of the valve arrangements 56 from the sealing position, to an open position, to open the liquid path 106. This is achieved once the pistons 102 are brought into abutment with the valve arrangements 56, during engagement of the cartridge 12 and the sonication chamber 14. Thus, liquid held in the reservoir 26 is permitted to flow over the pistons 102 and through the holes 104, to inner chamber 90. Dis-engagement of the cartridge 12 from the sonication chamber 14 provides the stoppers 60 of the valve arrangements 56 to return, under bias, to the sealing position, effectively closing the liquid path 106 and sealing the reservoir 26.

The engageable nature of the cartridge 12 and the sonication chamber 14, is made possible by a complimentary arrangement situated at an interface between the sonication chamber 14 and cartridge 12.

In the current embodiment, the sonication chamber 14 includes a pair of magnets 108 spaced apart and aligned to attract a pair of metal plates 110 positioned along the cartridge 12. Bringing the magnets 108 and metal plates 110 into proximity allows the attractive force of the magnets 108 to draw the metal plates 110 into abutment, to form the engagement. The complimentary arrangement may take various forms; such as a bayonet type arrangement, a threadedly engaged type arrangement or even a friction fit type arrangement. What is required is that the arrangement provides sufficient engaging force to hold the cartridge 12 and sonication chamber 14 together, and overcome the biasing force applied to the stoppers 60 of the valve arrangement 56, to open the flow path.

Figure 7:
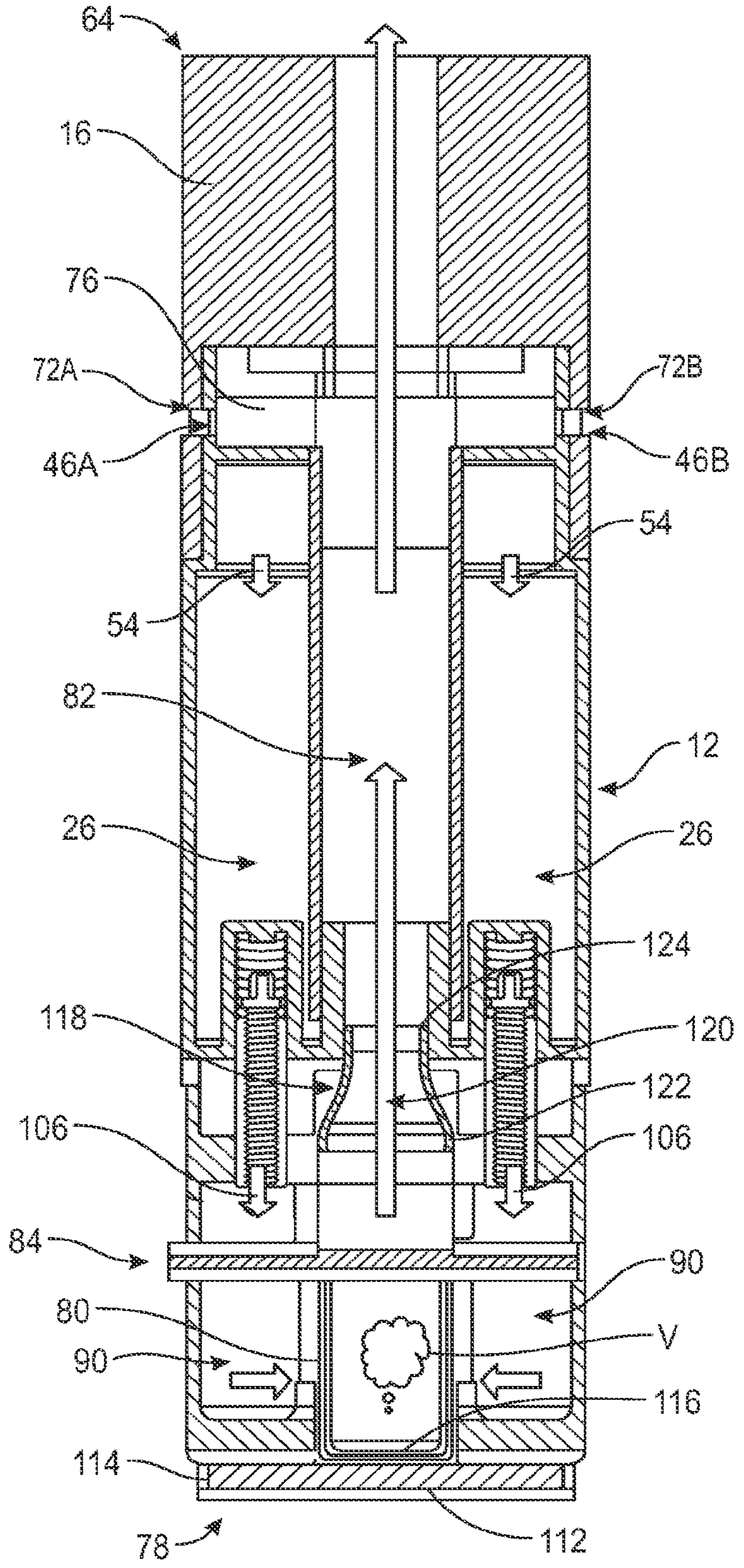
FIG. 7: shows a view from a side and in cross-section of the device of FIG. 1.

Turning now to FIG. 7. The ultrasonic oscillation arrangement 78 includes a piezoelectric disc 112 seated in a flexible sleeve 114 which is in proximity to the wick 80.

The wick 80 is placed in contact with an atomization surface 116 of the piezoelectric disc 112. The wick 80 is formed to have a capillary action to draw liquid placed in contact with the wick 80, and/or held in the inner chamber 90, to the atomization surface 116.

Unlike the use of a normal absorbent material, such as cotton, the wick 80 will draw the liquid to be atomized to the atomization surface 116, irrespective of the orientation of the personal ultrasonic atomizer device 10 itself.

Therefore, certain absorbent materials may allow liquid to drain away from the atomization surface 116, say for example where the device is completely inverted. The liquid will drain through the material under the influence of gravity and away from the surface 116. In this scenario the device, although powered and functioning, could not be used in the ordinary sense. Oscillation of the piezoelectric disc 112 would still take place, but there would be no liquid to atomize.

By using the wick 80, liquid will always be drawn to the atomization surface 116, even if the personal ultrasonic atomizer device 10 is completely inverted. Particularly useful for times when a user is horizontal, or lying down. The wick 80 construction, and physical properties ensure that saturation of the wick 80, by the liquid to be atomized, is always evenly distributed throughout the wick 80. Therefore, liquid cannot drain away (or in any direction) based on the orientation of the personal ultrasonic atomizer device 10.

To feed an amount of liquid to the inner chamber 90 for atomization, requires that the stoppers 60 of the valve arrangements 56 be moved against the biasing force applied by the biasing means 58 to open the liquid path 106.

This action is made possible by engaging the cartridges with the sonication chamber 14, while the member 16 is twisted to an open position, to release the vacuum and allow the liquid, held in the reservoir 26, to flow through the liquid path 106, over pistons 102 and through holes 104 to the inner chamber 90.

When a sufficient amount of liquid has entered the inner chamber 90, the member 16 may be twisted to the sealing position, to thus restore the vacuum and hold the liquid within reservoir 26.

The liquid now in the inner chamber 90 will then meet the wick 80 and be drawn to the atomization surface 116.

The ultrasonic oscillation arrangement 78 is interconnected to the energy storage arrangement 94 and computer 98. The computer 98 controls and regulates the oscillation of the piezoelectric disc 112. Thus, when the personal ultrasonic atomizer device 10 is activated the liquid brought into contact with the atomization surface 116 is atomized to form a vape (V).

The sonication chamber 14 includes at least one air inlet port 84 for supplying air from the surroundings to the inner chamber 90. The air supplied from the air inlet port 84 is directed away from the atomization surface 116, and toward the direction of the inhalation channel 82.

In the current embodiment the air inlet port 84 is shown as a tubular body having a cut-out portion located over, and orientated away from, the atomization surface 116.

The inhalation channel 82 is positioned over the atomization surface 116, such that any vape (V) generated by the oscillation arrangement 78 is fed to the inhalation channel 82.

Air introduced through the air inlet port 84 mixes with the vape (V) being generated from the atomization surface 116. The vape (V)/air fluid mixture then passes into the inhalation channel 82, when in use.

The inhalation channel 82 extends from the sonication chamber 14, through the internal bore 30 of the cartridge 12, and through the internal orifice 66, terminating at the trailing end 64 of the member 16. The inhalation channel 82 additionally includes a mouth piece (not shown) at the trailing end.

The inhalation channel 82 includes a frustoconical body 118. The frustoconical body 118 includes an internal passage 120, aligned in the similar direction as the inhalation channel 82, having a proximal end 122 and a distal end 124. The distal end 124 having a diameter less than that of the proximal end 122, such that the internal passage 120 reduces in diameter over the frustoconical body 118 length.

The frustoconical body 118 is positioned in alignment with the atomization surface 116, wherein the proximal end 122 is nearer the surface. As shown in FIG. 7 the air inlet port 84 is positioned between the atomization surface 116 and the frustoconical body 118.

The vape (V)/air fluid mixture which passes into the inhalation channel 82 is met by the frustoconical body 118. The reducing internal passage 120 increases the pressure of the fluid mixture which, in turn accelerates movement of the fluid mixture through the inhalation channel 82 and toward the mouth piece.

FIG. 7 shows slots 72A and 72B of the member 16 in alignment with the ducts 46A and 46B of the cartridge 12. When in alignment, air from the surroundings may flow to the reservoir 26.

The cartridge 12 and sonication chamber 14 may be disengaged. When disengagement occurs, the pistons 102 are withdrawn from abutment with the stoppers 60 of the valve arrangement 56. The stoppers 60 move to the sealing position under the force of the biasing means 58 and the reservoir 26 is sealed, thus preventing leakage of liquid from the reservoir 26.

Different cartridges 12 may be used interchangeably with the sonication chamber 14, without having to completely or partially discharge the reservoir 26 from liquid. Each cartridge 12 used and/or interchanged with the sonication chamber 14 is specifically coded and identifiable to the sonication chamber 14 through the cartridge 12 microchip 126.

The microchip 126 is brought into contact with the contact panel 86 when the cartridge 12 and sonication chamber 14 are engaged. The contact panel 86 provides communication between the data stored on the microchip 126 and the computer 98.

The computer 98 and the energy storage arrangement 94 form part of an electronic system for operating the personal ultrasonic atomizer device 10. The system includes, in addition to the computer 98 and the energy storage arrangement 94, a means for communication with an electronic device 130 and a Global Positioning System (GPS) module 132. The computer 98 operates the personal ultrasonic atomizer device 10.

Such operation may include permitting power from the energy storage arrangement 94 to power the personal ultrasonic atomizer device 10 or preventing power from the energy storage arrangement 94 to render the personal ultrasonic atomizer device 10 unusable.

Powering the personal ultrasonic atomizer device 10, includes providing a current to the electronic oscillation arrangement 78. The electronic oscillation arrangement 78, which includes the piezoelectric disc 112, cannot oscillate the piezoelectric disc 112 without a current, and without oscillation, there is no atomization of a liquid at the atomization surface 116.

The operation may be dependent on the nature of the data contained on a microchip 126 and/or the physical location of the personal ultrasonic atomizer device 10. In addition, the computer 98 may operate the personal ultrasonic atomizer device 10 according to any pre-programmed guidelines held within the computer 98 firmware or software.

The computer 98 may connect and communicate with an electronic device, through the means for communication with an electronic device 130. Typically, such communication will take place by connecting the personal ultrasonic atomizer device 10 to a program hosted on the electronic device 130.

The program may be used to operate the personal ultrasonic atomizer device 10, by passing commands to the computer 98.

In a use case, the communication will relate to determining the authenticity of the cartridge 12 being used with the personal ultrasonic atomizer device 10. The computer 98 is programmed to detect the use of a fake, or non-original, cartridge. And if such a fake cartridge was detected, the computer 98 would prevent power to the personal ultrasonic atomizer device 10, rendering it unusable.

The computer 98 may also record data of the cartridge 12, such as make, model, number and even flavour, and volume of the cartridge 12. By recording and storing this data, the computer 98 may operate the personal ultrasonic atomizer device 10.

Figure 9:
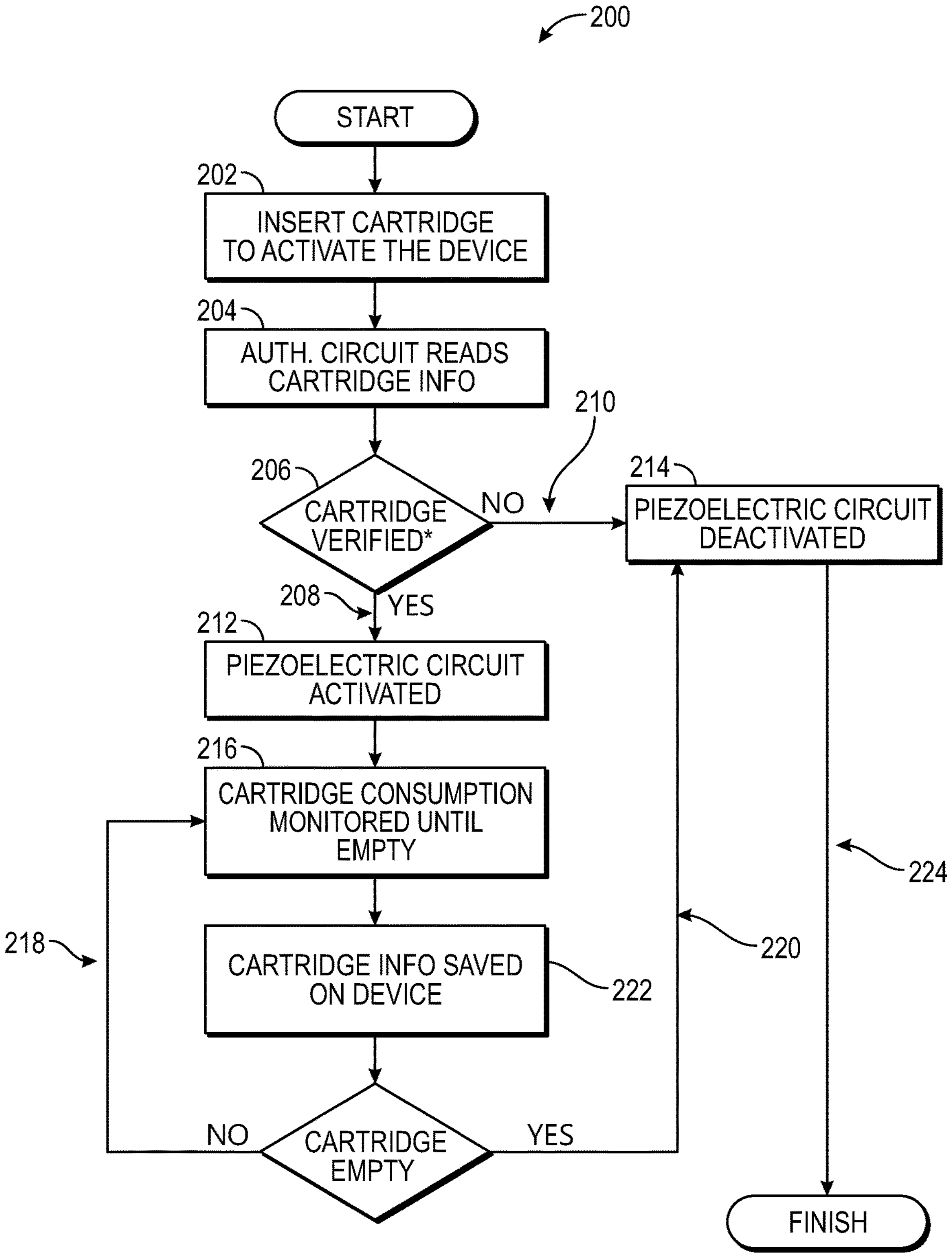

FIG. 9 shows a flow diagram 200, which depicts the steps in which the computer 98 will operate the personal ultrasonic atomizer device 10, based on data stored on the microchip 126.

Step one 202 involves the cartridge 12 being engaged with the sonication chamber 14. The engagement is such that the microchip 126 is brought into contact with the contact panel 86. Such contact provides a communication link between the microchip 126 and the computer 98. Information relating to the cartridge 12 make, model, number, flavour and volume is read by the computer 98. Step two 204 requires that the authenticity of the cartridge 12 is verified. Data specific to the cartridge 12 in a coded form is communicated to the computer 98. The computer 98 will run an algorithm designed specifically to identify cartridge 12 with corresponding codes matching the algorithm to ensure authenticity of the cartridge 12.

Step three 206, involves authenticating the cartridge 12. If the code on the cartridge 12 is compatible with the algorithms of the computer 98, a signal will be sent to activate the personal ultrasonic atomizer device 10. Such activation may involve permitting power from the energy storage arrangement 94 to the personal ultrasonic atomizer device 10, this is shown by arrow 208 (activate).

However, if the code is not compatible with the computer's 98 algorithm a signal will be sent to deactivate the personal ultrasonic atomizer device 10. Such deactivation may involve preventing power from the energy storage arrangement 94 to the personal ultrasonic atomizer device 10, this is shown by arrow 210 (deactivate). As referred to above, deactivation amounts to preventing power to the electronic oscillation arrangement 78. This in turn prevents oscillation of the piezoelectric disc 112 and no atomization can take place.

Step four 212 (activate). The signal to activate the personal ultrasonic atomizer device 10 may include a signal to activate the ultrasonic oscillation arrangement 78.

Alternatively, step four 214 (deactivate). The signal to activate the personal ultrasonic atomizer device 10 is not sent, and the ultrasonic oscillation arrangement 78 is not activated. In this instance, the operation 200 is ended, shown by arrow 224.

Only by replacing the cartridge 12 with a different cartridge 12 will the operation be re-started. This serves as an anti-counterfeiting deterrent, allowing only original cartridge 12 to function with the personal ultrasonic atomizer device 10.

Step five 216, the personal ultrasonic atomizer device 10 is used in accordance with ordinary normal use of the personal ultrasonic atomizer device 10. The computer 98 continually monitors the cartridge 12. The monitoring may include measuring the volume of liquid within the cartridge 12 during use, and measuring rate of consumption, to determine when the cartridge 12 is likely to be discharged of fluid.

If the cartridge 12 still contains fluid and is currently in use with the personal ultrasonic atomizer device 10, the personal ultrasonic atomizer device 10 will continue to operate in the ordinary normal way, this is depicted by arrow 218 (normal use).

When the cartridge 12 is discharged, a signal will be sent to the computer 98 to this effect. Such a signal will result in the deactivation of the ultrasonic oscillation arrangement 78 and the end of the personal ultrasonic atomizer device 10 operation. This is depicted by arrow 220 (discontinued use).

Step six 222, during normal ordinary use of the personal ultrasonic atomizer device 10, information related to the cartridge 12 is saved and stored on the computer 98. The information may be used in operating this, or other, cartridge 12.

The information stored on the computer 98, may include the make, model and volume of the reservoir 26 and the nature of the liquid as it relates to a cartridge 12. Additionally, the information stored may also include the amount of liquid which has been discharged from the reservoir 26 during the use of the personal ultrasonic atomizer device 10.

By measuring the amount of liquid discharged, the computer 98 may predict, based on the number of times the personal ultrasonic atomizer device 10 is activated, how much liquid is remaining in the reservoir 26. The amount of liquid remaining provides a guideline as to how much longer the device may be used with the cartridge 12 before the reservoir 26 is completely discharged and when operation must be prevented.

When cartridge 12 is removed, prior to all the liquid being discharged in the reservoir 26, the computer 98 will create a memory data entry to record the amount of liquid which remained in the cartridge 12. Once the cartridge 12 is re-inserted, and normal use continues, the computer 98 will recall the memory data of the amount of liquid remaining in the reservoir.

Operation of the personal ultrasonic atomizer device 10 will then only be permitted for as long as the remaining liquid would take to be depleted. Once this remaining fluid is depleted, the operation will be prevented.

This memory data recall will act as a tamper deterrent, wherein any additional liquid inserted to the reservoir 26 will not be used. Examples may include where a user attempts to refill the reservoir 26 using a syringe filled with liquid, to increase the use of a particular cartridge 12.

The computer 98 may also operate the personal ultrasonic atomizer device 10 by determining the physical location of the personal ultrasonic atomizer device 10, using either the Global Positioning System (GPS) module 132, or the Global Positioning System (GPS) module of the electronic device. Locating the device within certain predefined geo-locations results in the computer preventing power from the energy storage arrangement 94 to power the device. In such a scenario, the operation 200 of the personal ultrasonic atomizer device 10 will be similar to that depicted in FIG. 8.

Step three 206 will be replaced with a location confirmation relative to certain rules surrounding a predefined geolocation. Depending on the location of the device within the geolocation, the computer may operate the personal ultrasonic atomizer device 10 according to step four 212 (activate) as depicted by arrow 208 (activate) or alternatively step four 214 (deactivate) as depicted by arrow 210 (deactivate).

Over time, the computer 98 may require software updates to its processing systems.

Software updates may be communicated to the computer 98 in different ways. One such way to provide for an update is when the means for communicating with an electronic device 130 connects to the program on said electronic device. The program may contain the update and communicate this to the computer.

A further way in which an update may take place would be when the update data/information is contained on the microchip 126 of a cartridge 12 inserted into the device. The information is then transferred through the direct communication which is created when the microchip contacts the contact panel 86. The flow of data may then take place.

An even further way in which the computer 98 may be updated would be to place the contact panel 86 in contact with a dedicated updating system.

The dedicated updating system may be in any form which creates a physical connection between the contact panel 86 and an electronic device 130 which contains the update. Common examples of such devices include a docking station, or an electronic cable connected to an electronic device, such as a computer.

Once the physical connection is made, the data, or update, may be transferred to the computer 98, to update the computer 98.

While certain embodiments have been selected to illustrate the present invention, and specific examples have been described herein, it will be obvious to those skilled in the art that various changes and modifications may be aimed to in the specification. It will, therefore, be understood by those skilled in the art that the particular embodiments of the invention presented here are by way of illustration only and are not meant to be in any way restrictive; therefore, numerous changes and modifications may be made, and the full use of equivalents resorted to, without departing from the spirit or scope of the invention.

The invention claimed is:

1. A personal ultrasonic atomizer device, comprising
- a cartridge having a reservoir for holding a liquid to be atomized;
- a sonication chamber placed in fluid communication with the reservoir; and
- a member for controlling the amount of liquid flow into the sonication chamber;
  - wherein the reservoir includes at least one opening for providing air passage to the interior of the reservoir and at least one aperture for providing a flow path from the interior of the reservoir to the sonication chamber;

wherein the member is engaged with the cartridge to be movable between a sealed position, at which the at least one opening is closed, and a flow position, at which the at least one opening is open;

wherein liquid held in the reservoir is discharged to the sonication chamber once the member is in the flow position and the liquid is atomized in the sonication chamber, and liquid held in the reservoir remains in the reservoir when the member is in the sealed position.

2. The personal ultrasonic atomizer device as claimed in claim 1 which includes at least one slot through the member for providing an air passage.

3. The personal ultrasonic atomizer device as claimed in claim 1 wherein the member is movable relative to the cartridge, between the flow position and the sealed position, in at least one of a lateral, a vertical and a twist manner.

4. The personal ultrasonic atomizer device as claimed in claim 1 wherein the sonication chamber includes an atomization piece, having piezoelectrical ability, a flexible sleeve to receive the atomization piece, an electronic arrangement electrically coupled to the atomization piece for driving oscillation of the atomization piece, and a wick for directing fluid from the reservoir, to be atomized, in the sonication chamber to the atomization piece.

5. The personal ultrasonic atomizer device as claimed in claim 1 wherein the cartridge includes a microchip for storing data specific to the reservoir.

6. The personal ultrasonic atomizer device as claimed in claim 1 wherein the aperture includes a valve arrangement, biased to a closed position, to seal the aperture and restrict the flow path.

7. The personal ultrasonic atomizer device as claimed in claim 6 wherein a piston overcomes the bias of the valve arrangement, when placed in abutment therewith, to move the valve arrangement and open the aperture to open the flow path.

8. The personal ultrasonic atomizer device as claimed in claim 7 wherein liquid held in the reservoir flows through the flow path to the sonication chamber when the member is moved to an open position and when the piston is in abutment with the valve.

9. The personal ultrasonic atomizer device as claimed in claim 1 wherein the sonication chamber includes at least one air inlet port to introduce air to the sonication chamber.

10. The personal ultrasonic atomizer device of claim 9 wherein the at least one air inlet port is formed to orientate air introduced to the sonication chamber with a flow of atomized liquid exiting the sonication chamber.

11. The personal ultrasonic atomizer device of claim 9 wherein the at least one air inlet port is formed to introduce air to the sonication chamber co-linearly with a flow of atomized liquid exiting the sonication chamber.

12. The personal ultrasonic atomizer device as claimed in claim 11 wherein the at least one air inlet port includes an elongate tubular body having a sidewall extending between opposing ends and having a portion removed from the sidewall.

13. The personal ultrasonic atomizer device as claimed in claim 1 which includes a channel terminating in a first end received in the sonication chamber, and an opposite second end, formed as a mouth piece.

14. The personal ultrasonic atomizer device as claimed in claim 13 wherein the channel includes a cylindrical body, having a proximal end orientated toward the sonication chamber, a distal end orientated toward the mouth piece, and at least one stopper for altering the flow rate of a fluid passing through the channel.

15. The personal ultrasonic atomizer device as claimed in claim 1 which includes an electronic system for operating the personal ultrasonic atomizer device, wherein the electronic system is a component of the personal ultrasonic atomizer device and comprises a computer, an energy storage arrangement, and a communication system for communicating with an electronic device and a Global Positioning System (GPS) module.

16. The personal ultrasonic atomizer device as claimed in claim 15 wherein the computer includes a contact panel for receiving, and for providing communication with, a microchip.

17. The personal ultrasonic atomizer device as claimed in claim 16 wherein the communication system for communicating with an electronic device includes at least one of wireless communication circuitry, Bluetooth connectivity circuitry, Global System for Mobile Communication (GSM) communication circuitry, and a connector for placing the device in physical communication with the electronic device.

18. The personal ultrasonic atomizer device as claimed in claim 17 wherein the communication system communicates with a program provided on the electronic device.

19. The personal ultrasonic atomizer device as claimed in claim 18 wherein a physical location of the personal ultrasonic atomizer device is provided by the Global Positioning System (GPS) module.

20. The personal ultrasonic atomizer device as claimed in claim 19 wherein the computer operates the personal ultrasonic atomizer device based on the communication with the microchip according to at least one of the physical location of the personal ultrasonic atomizer device and according to the program on the electronic device.

* * * * *